United States Patent [19]

Brown

[11] 4,299,005
[45] Nov. 10, 1981

[54] APPLICATOR

[76] Inventor: Harold B. Brown, 2951 Village Dr., Marietta, Ga. 30062

[21] Appl. No.: 81,462

[22] Filed: Oct. 3, 1979

[51] Int. Cl.³ .......................... B05C 1/06; A47K 7/03
[52] U.S. Cl. .............................. 15/244 A; 15/104.94; 15/144 R; 401/262
[58] Field of Search ............ 15/104.94, 144 R, 144 B, 15/145, 184, 210 R, 244 R, 244 A, 244 C, 143 R; 401/98, 124, 202, 262

[56] References Cited

U.S. PATENT DOCUMENTS

| | | |
|---|---|---|
| 3,124,828 | 3/1964 | Barber et al. ...................... 401/202 |
| 3,491,397 | 1/1970 | Hesener ............................. 15/244 A |
| 3,568,237 | 3/1971 | Rhodes .............................. 15/244 A |
| 3,596,946 | 8/1971 | Burton ........................... 15/144 B X |
| 3,704,480 | 12/1972 | Whitaker .......................... 15/244 A |
| 3,771,190 | 11/1973 | Tischler et al. .................... 15/244 R |
| 4,078,865 | 3/1978 | Moser ................................ 401/202 |
| 4,171,171 | 10/1979 | Jones ................................. 401/262 |

*Primary Examiner*—Edward L. Roberts
*Attorney, Agent, or Firm*—Hill, Van Santen, Steadman, Chiara & Simpson

[57] ABSTRACT

An applicator adapted to neatly apply lotions, medicaments, and the like to the skin of a user reaches the entire back area of the user by hand manipulation of an elongated stem or handle pivotally connected to a head carrying an absorbent pad which is saturated with the lotion or medicament. The hands or clothing of the user need not contact the pad. A removable lid or cover on the head protects the saturated pad from contaminants, minimizes evaporation of the lotion, and isolates the pad to prevent the lotion from soiling surrounding material during non-use of the applicator. The stem or handle has telescoping sections extensible to a desired length and an eccentric lock secures the telescoped sections in fixed position. A stop limits the pivoting of the handle on the head to maintain a pushing angle relative to the head. The head and handle are separable to provide a compact knock-down package and to accommodate replacement of the head.

7 Claims, 7 Drawing Figures

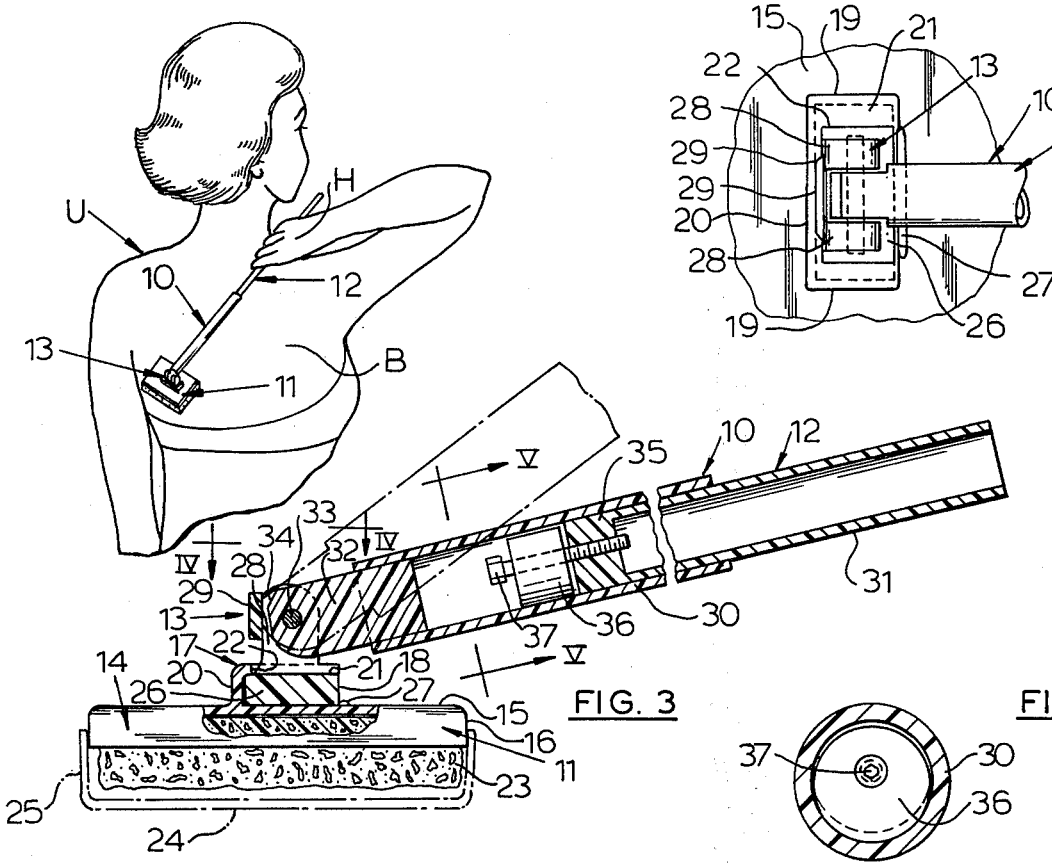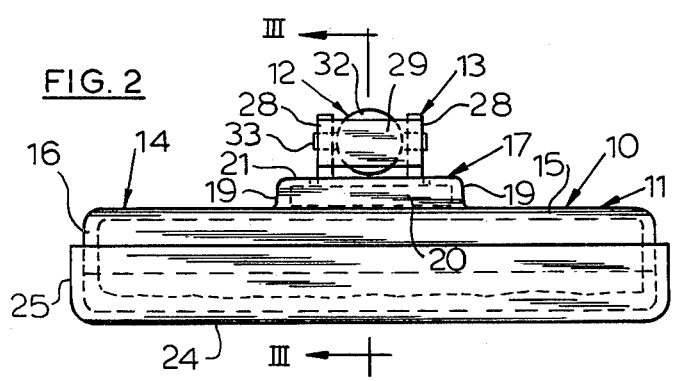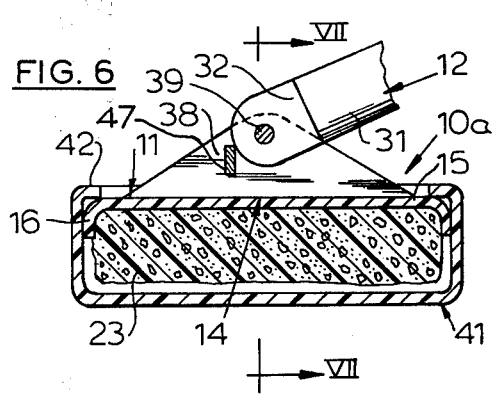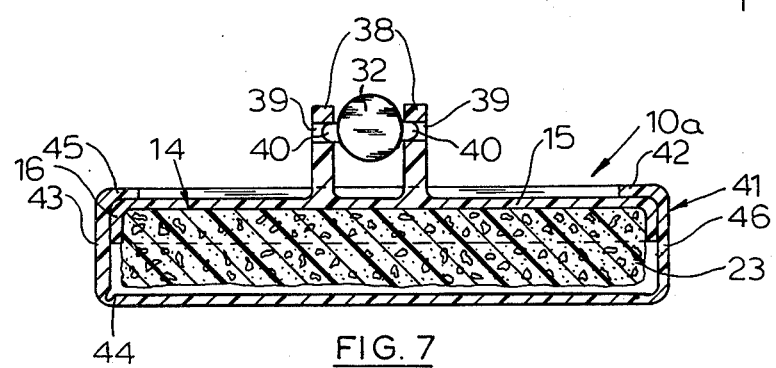

APPLICATOR

FIELD OF THE INVENTION

This invention relates to the art of storing and neatly applying lotions, medicaments, and the like to the human body without soiling clothes, and particularly deals with a suntan lotion applicator having a head carrying an absorbent pad saturated with the lotion and protected by a removable cover to isolate the lotion and to present a clean surface of the pad to the skin and manipulated by an extensible handle pivoted to the head.

BACKGROUND OF THE INVENTION

Long handled scrubbers or back brushes conventionally have the elongated handle fixed to the brush head. Attempts to use such devices to apply lotions, such as suntan ointments, medicaments and the like to the back of a user waste the lotion, soil clothing, pick up sand and other debris and are not conveniently carried in a purse or pocket of the user. It would thus be an improvement in the art to provide an applicator saturated with the material to be applied to the body and protected during non-use by a cover and which can be hand manipulated by a pivoted handle that is selectively extended to a convenient length.

SUMMARY OF THE INVENTION

According to this invention there is provided a hand operated applicator which can be controlled to easily reach all areas of the human body to neatly and selectively apply sunscreening formulations, skin treating medicaments, medications and the like without waste or contamination or soiling of clothing or the hands. The invention includes a head carrying an absorbent pad or sponge of convenient size to provide an appreciable applying area of say 2½ by 3½ inches. A telescoping stem or handle is pivoted on the head and its pivotal movement is limited so that the pad will always be propelled by the stem. The telescoped elements of the handle are easily locked in desired extended position by relative rotation. A preferred extended length for the handle is about 10 to 14 inches with a collapsed length of about one half the extended length. The head and handle are preferably formed of plastics material. A polyolefin resin is suitable for the head while a stiffer polyvinyl chloride resin is suitable for the handle.

The handle is separable from the head to provide a compact knock-down condition and to accommodate replacement of the head and pad.

Various types of covers and lids can be provided for the head to isolate the pad against contamination by sand and the like, to minimize evaporation of the saturant, and to prevent the lotion from soiling surrounding items, such as when the applicator is carried in a handbag or purse.

It is then an object of this invention to provide an applicator which is easily manipulated by hand without soiling the hand to reach all portions of the human body for neatly and smoothly depositing a coating of material on the skin and which covers the material when not in use.

Another object of this invention is to provide an applicator for applying lotions, medicaments and the like to the human body which has a head carrying a pad and closed by a removable lid or cover to protect the pad and is manipulated by a handle pivoted thereon with the pivoting movement limited to facilitate transmission of a pushing thrust from the handle to the head.

Another object of the invention is to provide a suntan lotion applicator which has a sponge secured in a box with a removable cover and has an elongated stem pivoted thereon to direct the pad as desired over the body of a user.

Other and further objects of this invention will become apparent to those skilled in this art from the following detailed description of several preferred embodiments of the invention showing a best mode of the invention.

ON THE DRAWINGS

FIG. 1 is a pictorial illustration of the applicator of this invention in use to apply lotion to the back of the user;

FIG. 2 is an end elevational view of the applicator with a cover applied thereto;

FIG. 3 is a longitudinal cross-sectional view, with parts in side elevation taken substantially along the line III—III of FIG. 2 and showing in dotted lines the limited pivotal position of the stem;

FIG. 4 is a fragmental plan view along the line IV—IV of FIG. 3;

FIG. 5 is a cross-sectional view along the line V—V of FIG. 3;

FIG. 6 is a fragmentary side elevational view with parts in transverse cross-section of a modified embodiment of the invention; and FIG. 7 is a cross-sectional view along the line VII—VII of FIG. 6 with dotted line positions showing the opening of the cover.

AS SHOWN ON THE DRAWINGS

The applicator 10 shown in FIGS. 1 to 4 of this invention has a head 11, an extensible handle 12, and a pivot assembly 13 joining the head and handle.

As shown in FIG. 1 the applicator 10 is manipulated by the hand H of a user U grasping the handle 12 to propel the head 11 over the back B of the user.

The head 11 as best shown in FIGS. 2 and 3 includes a tray or box-like member 14 preferably formed of plastics material and having a flat back 15 and peripheral sidewalls 16. The back wall 15 has integrally molded or cemented thereon an upstanding bracket 17 providing a pocket to receive the pivot mounting. This bracket 17 has an open front 18, upstanding sidewalls 19, 19 and an upstanding back wall 20 between the sidewalls 19, 19. A flat top wall 21 extends from the side and back walls and has a central rectangular recess or groove 22 communicating with the open front 18.

The tray of box 14 houses a resilient absorbent pad such as 23 snugly fitting the sidewalls 16 and projecting therebeyond. The pad is preferably secured in the box by adhesive or the like or can be pressed into a tight fitting relationship with the box to be retained by friction therein. This pad is saturated with any desired fluid such as a suntan lotion, a sunburn treating ointment, or the like to be applied to the skin of the user U.

The box 14 is closed by a lid or cover 24 overlying the pad 23 and having peripheral sidewalls 25 surrounding the sidewalls 16 of the box in friction engagement therewith.

It will thus be understood that the head 11 is a separate unit closed by a cover for conveniently carrying in a pocket, handbag or purse of the user without exposing the pad.

The bracket 17 releasably receives the base or foot 26 of the pivot mounting 13. This base 26 is inserted into the pocket of the bracket through the opening front side 18 thereof to be bottomed against the back wall 20. A rib, bead, or the like 27 is preferably molded on the wall 15 in front of the bracket to engage the front face of the base or foot 26 for retaining the same in the pocket of the bracket.

The base or foot 26 has a pair of laterally spaced upstanding ears 28, 28 projecting freely through the slot or recess 22 in the top of the bracket. A strap 29 spans the space between the ears and is integrally affixed to the front side edges of these ears near the tops thereof to provide a pivot stop as will be more fully hereinafter described. The base 26, ears 28, and strap 29 can be a one piece molded plastics material unit.

The handle 12 includes two telescoped tubular components 30 and 31. The component 30 receives a plug 32 in the end thereof adjacent the head 11 which projects from the component freely between the ears 28, 28 of the pivot mounting. A pin 33 extends transversely through the projecting end of the plug 32 into the ears 28, 28 to pivotally connect the plug 32 with the pivot mounting carried in the bracket 17. The plug 32 has a rounded front wall 34 adapted to abut the strap 29 and limit the swinging movement of the handle 12 as shown in dotted lines in FIG. 3 so that the handle 12 will always be at an angle to the head 11 for exerting a pushing and pulling action on the head. The stop also limits swinging of the head of an angular position such that the edges of the sidewalls 16 of the box 14 could scratch the skin of the user.

The components 30 and 31 of the handle 12 and the plug 32 carried by the component 30 are preferably formed of molded plastics material.

The handle component 31 has a closed end 35 telescoped in the component 30. A cylindrical plastics material head 36 is eccentrically mounted on this closed end 35 for rotation about a pin 37 secured in the end 35. The arrangement is such that rotation of the component 31 in the component 30 will wedge lock the head 36 in the component 30 for holding the component 31 at the desired contracted or extended position in the component 30. The head 36 is also preferably a molded plastics material member.

When the base or foot 26 of the pivot mounting is removed from the bracket 17 the components of the handle 12 can be telescoped to a compact condition easily fitting the pocket, purse or handbag of a user.

From the above description it should be understood that the applicator 10 can be easily assembled for use with the handle extended to a convenient length to be pushed and pulled for rubbing the sponge or pad 23 over selected parts of the body without exposing the hands of the user to the lotion saturating the pad 23. The handle can be guided so that the pad will not contact clothing, such as a swimming suit worn by the user.

In the modified embodiment 10a shown in FIGS. 6 and 7 the box or tray 14 of the head 11 has a pair of upstanding ears 38, 38 molded directly on the back wall 15 thereof. These ears are generally triangular in shape with an apex at the transverse centerline of the box 14. Each ear has an opening 39 therethrough at the apex. The plug 32 of the handle component 31 fits freely between the ears 38, 38 but instead of receiving a pin such as 33 therethrough, it has integral molded beads 40 projected laterally from the sides thereof fitting in the holes 39. The arrangement is such that the ears 38, 38 can be spread to accommodate snapping of the beads 40 in the holes 39 thereby providing a releasable pivot connection between the head 11 and the handle 12.

The box or tray 14 of the modification shown in FIGS. 6 and 7 receives an envelope type cover 41 which slides over the sidewalls of the box and has top flanges 42 riding on the back 15 of the box. This slide-on cover has a closed end wall 46 at one end thereof. The opposite end of the cover 41 has a lid 43 swingable about a fold line 44 to open and close the end of the cover opposite the wall 46. Thus the cover 41 can slide onto the box 14 to cover the pad 23 and the lid 43 can be moved to the closed position as shown in solid lines in FIG. 7 to provide a complete envelope for the pad. The lid 43 is retained in closed position by a lip 45 fitting over the back wall 15 of the box.

A strap 47 spans the ears 38, 38 to engage the plug 32 for limiting the swinging movement of the handle 12 as in the FIGS. 1 to 5 embodiment.

From the above descriptions it will be readily understood that this invention provides a hand manipulated pad for applying lotions, ointments and the like to selected portions of the body without soiling the hands or clothing of the user wherein the ointment to be applied is closed in a container until needed and wherein handle and head components are separable to provide a compact carrying condition.

I claim as my invention:

1. An applicator manipulated by the hand of a user to selectively apply fluids to all portions of the skin of a user which comprises a head, an elongated handle pivoted on said head, means limiting swinging of the handle to less that a quadrant from a position substantially parallel with the head to an inclined angle position relative to the head for causing the handle to transmit a pushing and pulling action on the head, a resilient absorbent pad carried by the head and presenting a surface area for rubbing on the skin of a user, and a removable cover on the head isolating the pad during periods of non-use.

2. The applicator of claim 1 wherein said head is a tray having a back wall and peripheral sidewalls, and said removable cover has peripheral sidewalls surrounding said tray sidewalls in friction engagement therewith.

3. The applicator of claim 1 wherein said head is a tray having a back wall and peripheral sidewalls, and said removable cover has peripheral sidewalls with top flanges, one of said cover sidewalls being a lid swingable about a fold line along an edge connecting said sidewall to said back, said cover sliding onto said tray wherein said top flanges ride on said tray back and said cover being moved to a closed position providing a complete envelope for said pad.

4. The applicator of claim 1 wherein said head is provided with a bracket for receiving said pivot mounting, said pivot mounting having a foot and a pair of laterally spaced apart upstanding ears, said foot being removably receivable in said bracket, said handle having an end portion projecting from said handle freely between said ears and a pin connecting said end portion and ears.

5. The applicator of claim 1 wherein said handle has telescoped inner and outer tubular components, said inner component having a closed end, a pin projecting from said closed end, and a head rotatably mounted on said pin with a periphery in eccentric relation therewith to wedge lock the components at a desired telescoped position when said components are relatively rotated.

6. The applicator of claim 1, wherein the head has a pair of laterally spaced apart upstanding ears of generally triangular shape with an apex at the transverse center line of said head, each of said ears having an opening therethrough at the apex thereof, said handle having an end portion projecting freely between said ears, said end portion having a pair of integral beads projecting laterally thereof fitting in said openings in said ears, said ears being spreadable to accommodate snapping of the beads into said openings thereby providing a releasable pivot connection between said head and said handle, and said means limiting swinging of the handle is a strap bridging said ears engaging said end portion.

7. An applicator for applying suntan lotions and the like to the skin of a user without soiling clothes which comprises a tray with a back wall having front and back faces, a continuous upstanding peripheral side wall depending from the front face, and a pair of spaced upstanding ears projecting from the back face, a removable cover having a continuous upstanding peripheral side wall sized for surrounding the peripheral side wall of said tray in frictional engagement therewith, a resilient absorbent pad filling said tray and projecting beyond the peripheral side wall of the tray into the cover, said tray and cover forming a closed compartment isolating the pad against contamination and minimizing evaporation of lotion or the like in the compartment, a handle having an end projecting between said ears, pivot means connecting said end and ears accommodating swinging of the handle to a position substantially parallel with said back wall of the tray, and a stop limiting swinging of said handle from said parallel position to an upright inclined angle position relative to said back wall of the tray for exerting a pushing and pulling action without permitting tilting of the tray sufficiently to engage the edge of the peripheral side wall thereof against the skin of the user.

* * * * *